United States Patent [19]

Teves

[11] Patent Number: 5,125,900
[45] Date of Patent: Jun. 30, 1992

[54] DEVICE FOR HEATING AND PRESSURIZING FLUID-FILLED CONTAINERS

[76] Inventor: Leonides Y. Teves, 623 39th St., West Bradenton, Fla. 34205

[21] Appl. No.: 587,264

[22] Filed: Sep. 24, 1990

[51] Int. Cl.$^5$ ............................................. A61F 7/12
[52] U.S. Cl. ................................. 604/114; 128/403; 604/142
[58] Field of Search ............... 604/113, 114, 141, 142, 604/146, 131; 128/384, 399, 400, 403, DIG. 24, 402, DIG. 20; 606/27, 31

[56] References Cited

U.S. PATENT DOCUMENTS

| 2,185,692 | 1/1940 | McCleary | 128/403 |
| 3,548,819 | 12/1970 | Davis et al. | 128/402 |
| 3,717,145 | 2/1973 | Berndt et al. | 128/402 |
| 3,901,222 | 8/1975 | Sconce | 128/402 |
| 4,702,235 | 10/1987 | Hong | 128/402 |
| 4,736,088 | 4/1988 | Bart | 128/402 |
| 4,804,367 | 2/1989 | Smith et al. | 604/113 |
| 4,808,159 | 2/1989 | Wilson | 604/113 |
| 4,868,898 | 9/1989 | Seto | 128/403 |
| 4,934,336 | 6/1990 | White | 604/113 |
| 4,981,135 | 1/1991 | Hardy | 604/403 |

Primary Examiner—C. Fred Rosenbaum
Assistant Examiner—Sharon Finkel
Attorney, Agent, or Firm—Joseph C. Mason, Jr.; Ronald E. Smith

[57] ABSTRACT

A device that wraps around a flexible bag containing fluid to warm the fluid and to pressurize the bag so that warmed fluid flows from the bag at a rate dependent upon the amount of pressure applied to the bag. The device includes a heating element that may be set at a preselected temperature and an inflatable bladder that may be inflated to a preselected pressure.

6 Claims, 3 Drawing Sheets

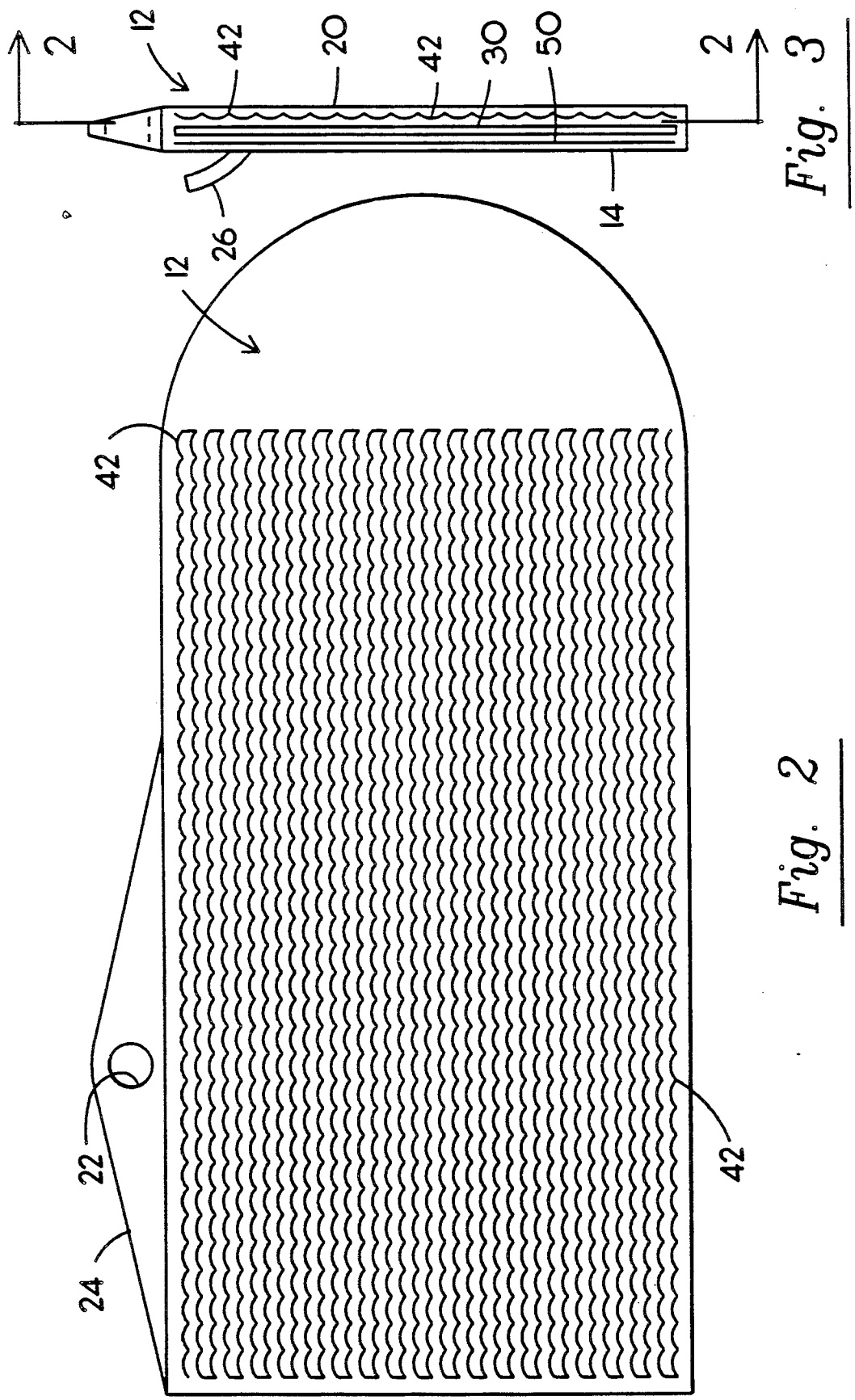

DEVICE FOR HEATING AND PRESSURIZING FLUID-FILLED CONTAINERS

TECHNICAL FIELD

This invention relates, generally, to medical surgical appliances. More particularly, it relates to a device that warms blood in a container and which provides pressure to pump the warmed blood from the container.

BACKGROUND ART

Patients in hospital wards or operating theaters from time to time require an infusion or transfusion of blood, blood products, or other fluids. In many cases, it is critical to maintain the patient's temperature at its optimal level to ensure the continued function of the patient's brain, heart, kidneys and other vital organs. For example, where a patient has lost a lot of blood or other body fluids as a result of trauma or where a patient requires replacement of large volumes of such fluids during surgery, it is critical that the replacement fluids be introduced into the patient's body at or near the patient's normal body temperature. The introduction of relatively large volumes of fluids at a low temperature has the effect of rapidly inducing hypothermia and the concomitant failure of said vital organs.

Blood and other fluids are commonly supplied in flexible containers known as intravenous (IV) bags. Typically, the bag is held in an elevated position on a pole and the contents thereof drip into the patient's veins slowly. The fluids are not normally heated because the slow rate of infusion does not result in a catastrophic lowering of body temperature, and the volume of fluid so introduced is usually quite low.

Devices for heating fluids have been developed, as have devices for pumping fluids, but the art contains no teachings or suggestions concerning combination devices that heat and pump blood in and from, respectively, containers such as IV bags.

DISCLOSURE OF INVENTION

The present device includes a flexible, flat, belt-like base member having a heating element and an inflatable bladder embedded therein. The device is wrapped around a flexible fluid-holding container such as an IV bag and is held in that position by suitable fastening means. A hand-operated pumping means is squeezed a number of times as required to pressurize the bladder so that the device squeezes the IV bag and thereby pressurizes it so that the fluid therein will flow therefrom at a rate proportional to the amount of pressure thereby supplied. A pressure gauge enables the pressure to be brought to the desired level. A rheostat controls the temperature of the heating element so that the device and hence the contents of the bag about which it is wrapped may be warmed to at least the patient's body temperature, and a temperature gauge facilitates monitoring of the temperature.

The primary object of this invention is to provide the world's first combination device for heating and pressurizing blood, blood products, or other fluids while said fluids are in an IV or similar bag.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 2 is a sectional view taken along line 2—2 in FIG. 3;

FIG. 3 is a sectional view taken along line 3—3 in FIG. 1;

BEST MODES FOR CARRYING OUT THE INVENTION

Figure 1:
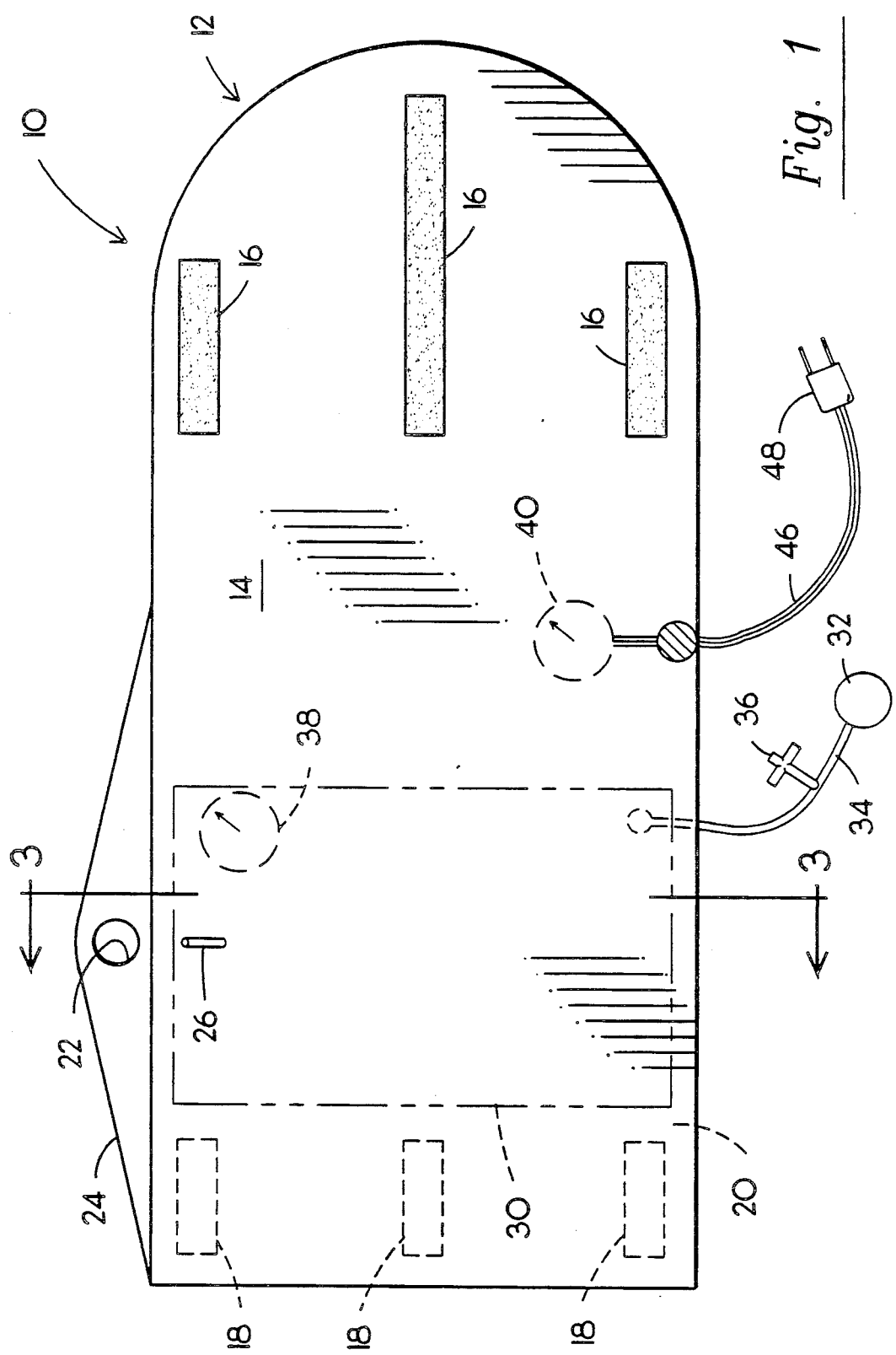
FIG. 1 is a top plan view of an exemplary embodiment of the device.

Referring now to FIG. 1, it will there be seen that an embodiment illustrative of this invention is denoted as a whole by the reference numeral 10.

Figures 4, 5:
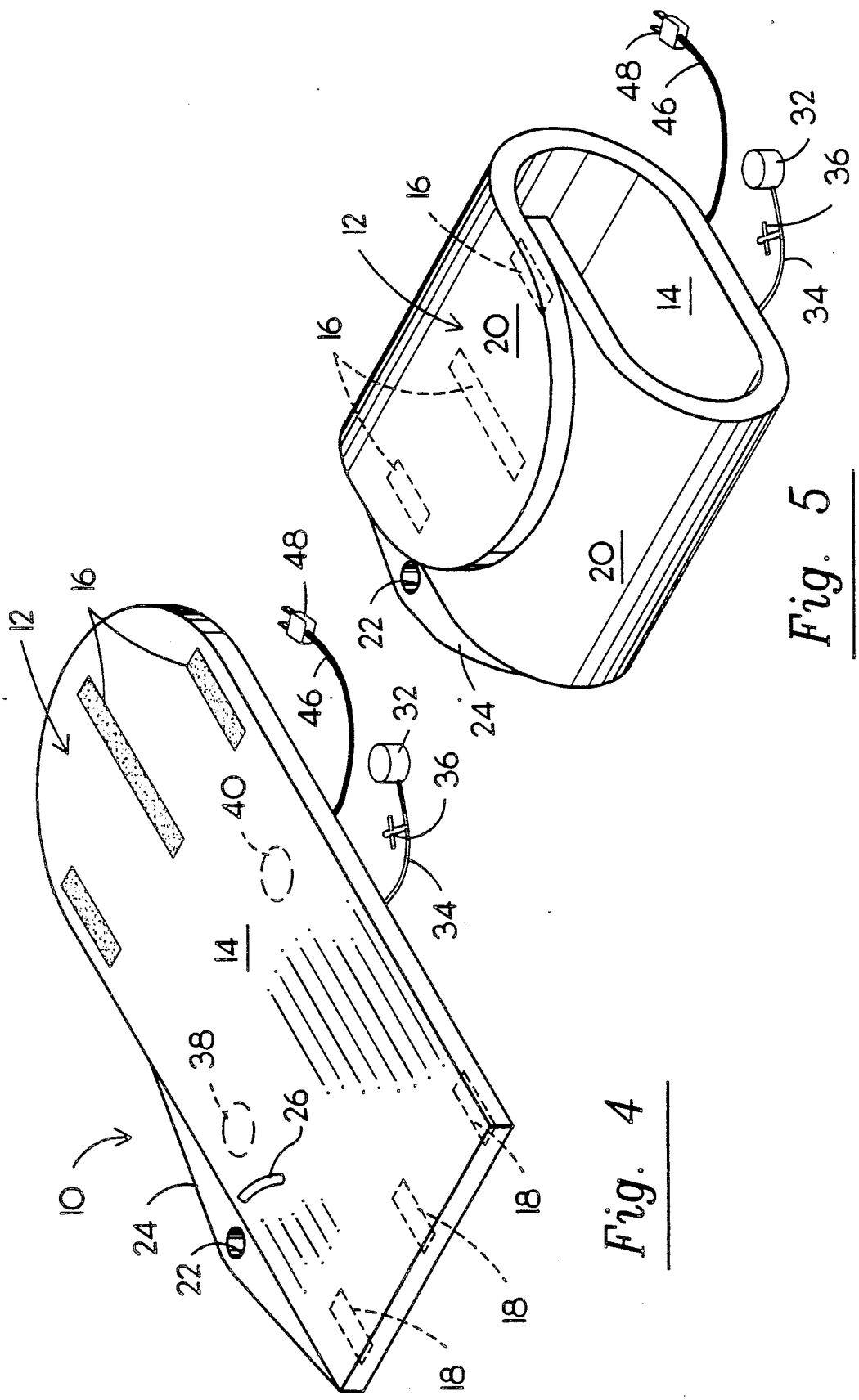
FIG. 4 is a perspective view of the exemplary embodiment when in its open configuration.
FIG. 5 is a perspective view of said embodiment in its closed or operative configuration.

The combination pump and heater 10 includes a flat, flexible base 12 having an inner surface 14 upon which is fixedly secured a plurality of Velcro fastening means 16. A plurality of complemental Velcro fastening means 18 is similarly secured to the outer surface 20 of said base 12. This enables the device to be configured as shown in FIG. 5, i.e., fastening means 16 are brought into overlying relation to fastening means 18 to wrap the device around a flexible bag such as an IV bag containing blood, blood products, glucose, or other fluids.

A thumb hole 22 formed in flap 24 and hook 26 which is secured to inner surface 14 are provided to facilitate releasable mounting of the device 10 to a support means such as an IV pole when device 10 is not in use.

An air bladder 30 is positioned in sandwiched relation between inner surface 14 and outer surface 18; when inflated, it expands and squeezes device 10 against the IV bag or other flexible bag about which it is wrapped to thereby provide a head of pressure that increases the flow rate of fluids from such bag relative to the flow rate achieved with gravity. Inflation is achieved by manual squeezing of a flexible, bulbous member 32 that is in fluid communication with the interior of bladder 30 through rubber hose 34. A "T"-shaped valve 36 facilitates release of air from bladder 30 when the transfusion has been completed.

Pressure gauge 38 is fixedly secured to the outer surface 20 of the device; it is in fluid communication with the interior of bladder 30 and enables the health care professional to avoid under and overpressurization.

A temperature gauge 40 is also mounted to the exterior surface 20 of the device; it enables the health care professional to monitor the temperature of the device 10. Heat is supplied to device 10 by heating element 42 (FIGS. 2 and 3); as shown in FIG. 1, the amount of current supplied to the heating element 42 is under the control of a rheostat 44 or other suitable control means. Cable 46 or other suitable conductor extends between said rheostat 44 and an AC adaptor 48. The temperature range of the heating element 42 is preferably 98-120 degrees F.

A layer of insulating foil 50 (FIG. 3) helps prevent heat loss to the atmosphere. FIG. 3 also shows that bladder 30 is sandwiched between said foil 50 and heating element 42. Said element 42 is near the inner surface 20 and no insulating means is positioned between it and said inner surface so that maximum heat transfer is achieved in the direction of the bag about which device 10 is wrapped.

FIGS. 4 and 5 provide perspective views of the device in its open and closed positions, respectively; all parts thereof have previously been described.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. An appliance for warming and pressurizing fluid contained in a flexible bag, comprising:
   a base member having a length sufficient to wrap about said bag;
   fastening means for releasably securing said base member to said bag when wrapped thereabout;
   a heating element positioned within said appliance;
   an inflatable bladder positioned within said appliance;
   means for selectively controlling the temperature of said heating element; and
   means for selectively controlling air pressure within said bladder;
   whereby fluid is introduced into a patient at a preselected temperature and flow rate when said appliance is wrapped about said bag.

2. The appliance of claim 1, further comprising an insulating foil positioned within said base member.

3. The appliance of claim 2, wherein said bladder is positioned in sandwiched relation between said insulating foil and said heating element.

4. The appliance of claim 3, wherein said insulating foil is positioned near an outer surface of said device and wherein said heating element is positioned near an inner surface of said device so that heat generated by said heating element is primarily transferred to the bag about which the base member is wrapped.

5. The appliance of claim 4, wherein said means for selectively controlling the temperature of said heating element includes a rheostat and a temperature gauge positioned on said outer surface of said base member for displaying the instantaneous temperature of said heating element.

6. The appliance of claim 5, wherein said means for selectively controlling the air pressure within said bladder includes a bulbous pumping means for manually pressurizing said bladder, a pressure gauge for displaying the pressure within said bladder, and a pressure release means for deflating said bladder.

* * * * *